(12) United States Patent
Allen-Hoffmann

(10) Patent No.: US 6,964,869 B2
(45) Date of Patent: Nov. 15, 2005

(54) METHOD AND COMPOSITION FOR SKIN GRAFTS

(75) Inventor: B. Lynn Allen-Hoffmann, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 85 days.

(21) Appl. No.: 10/131,977

(22) Filed: Apr. 24, 2002

(65) Prior Publication Data

US 2002/0192196 A1 Dec. 19, 2002

Related U.S. Application Data

(63) Continuation of application No. 10/299,938, filed on Nov. 19, 2002, which is a continuation-in-part of application No. 09/844,194, filed on Apr. 27, 2001, now Pat. No. 6,495,135, which is a continuation of application No. 09/769,124, filed on Jan. 24, 2001, now Pat. No. 6,485,724, which is a continuation of application No. 09/114,557, filed on Jul. 13, 1998, now Pat. No. 5,989,837.

(60) Provisional application No. 60/286,169, filed on Apr. 24, 2001.

(51) Int. Cl.$^7$ .......................... C12N 5/08; C12N 5/00; A01N 1/00; A01N 63/00; A61F 2/10

(52) U.S. Cl. ................. 435/371; 435/1.1; 435/402; 435/408; 424/93.21; 424/93.7; 623/15.12

(58) Field of Search .................. 424/93.7, 93.21; 435/1.1, 371, 402, 408; 623/15.12

(56) References Cited

U.S. PATENT DOCUMENTS

5,610,007 A    3/1997    Auger et al.
5,989,837 A    11/1999    Allen-Hoffmann et al.
6,214,567 B1    4/2001    Allen-Hoffmann et al.

FOREIGN PATENT DOCUMENTS

EP    0780 469 A1    6/1997
WO    WO 99/43787    9/1999

*Primary Examiner*—Hankyel T. Park
(74) *Attorney, Agent, or Firm*—Quarles & Brady LLP

(57) ABSTRACT

A chimeric skin comprising immortalized human keratinocyte cells cocultured with donor keratinocytes is disclosed.

20 Claims, 9 Drawing Sheets

Collagen solution and dermal fibroblasts are prepared and added to the transwell Collagen gel contracts in 4-7 days Day 0- Keratinocytes plated Day 4- Raft is lifted to air interface with cotton pads Day 9- Appearance of stratified skin equivalent, full stratification by day 15

Histology and GFP expression in organotypic cultures *in vitro* after harvest (day 16)

Collagen solution and dermal fibroblasts are prepared and added to the transwell Collagen gel contracts in 4-7 days Day 0- Keratinocytes plated Day 4- Raft is lifted to air interface with cotton pads Day 9- Appearance of stratified skin equivalent, full stratification by day 15

Histology and GFP expression in organotypic cultures *in vitro* after harvest (day 16)

METHOD AND COMPOSITION FOR SKIN GRAFTS

CROSS-REFERENCE TO RELATED APPLICATION

The application is a continuation-in-part of U.S. Ser. No. 09/844,194, filed Apr. 27, 2001, now U.S. Pat. No. 6,495,135, incorporated herein by reference in its entirety, which is a continuation of U.S. Ser. No. 09/769,124, filed Jan. 24, 2001, now U.S. Pat. No. 6,485,724, issued Nov. 26, 2002, which is a continuation of U.S. Ser. No. 09/114,557, filed Jul. 13, 1998, now U.S. Pat. No. 5,989,837, issued Nov. 23, 1999, which is a continuation of U.S. Ser. No. 10/299,938, filed Nov. 19, 2002. The application also claims priority to U.S. provisional patent application No. 60/286,169, filed Apr. 24, 2001, incorporated herein by reference in its entirety.

STATEMENT REGARDING FEDERALLY SPONSORED RESEARCH OR DEVELOPMENT

This invention was made with United States government support awarded by the following agency: NIH AR40284. The United States has certain rights in this invention.

BACKGROUND OF THE INVENTION

The skin is the largest organ in the human body and functions as a protective barrier against the agents, such as infectious agents, in the external environment, and as a waterproof barrier that maintains fluid homeostasis and prevents evaporation of tissue moisture. Intact skin prevents local infection of the dermis or other underlying tissue with microorganisms. If unchecked, such local infections can become invasive and can result in sepsis or systemic infection.

The temporary loss of skin often results in mortality or morbidity. Widespread loss of skin integrity is most often associated with major burns. The importance of the barrier function of skin is demonstrated by the fact that for a given age, mortality is directly related to burn size. Current standards of care recommend resurfacing of the patient as soon as possible to restore fluid homeostasis and barrier function.

Burn patients are most often resurfaced with autologous skin grafts. Autologous skin grafts techniques are widely used, but frequently fail. For example, a patient with large burns may not have sufficient donor skin available to cover the recipient site.

Two major alternative patient salvage techniques are currently available. One is to completely excise all the burned tissue and cover the patient with a temporary epidermis. INTEGRA (Johnson and Johnson, New Brunswick, N.J.) is a neo-dermis bilayer having an inner layer of bovine collagen and chondroitin-6-sulfate and an outer layer of silicone. After neo-dermal angiogenesis 14 to 21 days later, the silicone outer layer is surgically removed and the patient is resurfaced with thin, widely meshed autografts. The thin autografts offer the distinct advantage of allowing limited donor sites to heal and be serially harvested. Although the burn community has embraced INTEGRA, the susceptibility to infection has limited its use in patients with dirty or infected burn wounds (1). The other major limiting factor has been donor site availability. Patients with catastrophic burn injury may not have sufficient donor site available despite the obvious advantage of requiring much thinner autografts.

The second commonly employed technique is to excise the burn wound and to provide a temporary dermal/epidermal cover of cadaver skin to restore the skin's barrier function. Autologous keratinocytes are harvested and placed into culture. EPICEL (Genzyme Corporation, Cambridge, Mass.), the only commercially available permanent skin replacement, forms keratinocytes 2 to 6 cell layers thick attached to fine mesh gauze. These autografts are available in 3 to 4 weeks from the time of biopsy. In the case of large burns, this timetable often coincides with development of burn wound sepsis. Bacterial contamination and other factors cause high failure rates of EPICEL that are not seen with traditional split-thickness skin grafts (2).

Further advances in burn wound care may come from the arena of tissue engineering. One proposal has been to restore the barrier function with chimeric cultures of autologous keratinocytes mixed with established allogeneic cell cultures (3, 4). This could permit earlier wound coverage by significantly decreasing the time required for definitive culture formation. Slower permanent resurfacing of the skin would occur with autologous keratinocytes as the allogeneic cells are rejected. One major obstacle is the need for an established, cultured, and tested allogeneic keratinocyte line. This has heretofore been impractical as keratinocytes senesce in culture and new keratinocyte lines would have to be continually established and tested.

Skin is composed of two layers, the dermis and the epidermis. The dermis is a connective tissue containing fibroblasts embedded in a matrix of collagen and elastic fibers. The epidermis, in contrast, consists primarily of cells with little connective tissue.

Keratinocytes are the major cellular component of the epidermis and comprise about 80% of the cells in adult human skin. They are the epidermal component responsible for providing the skin's barrier, reparative, and regenerative properties. Their name derives from their predominant cytoskeletal component, keratins. Keratins are the subunits of keratin filaments and are divided into two types: type I (acidic) keratins and type II (basic or neutral) keratins. All epithelia express type I and type II keratins, which range in molecular weight from 40 kDa to 70 kDa. Different epithelial tissues express specific pairs of keratins. Heterodimers of type I and II keratins form intermediate filaments that confer tensile strength and structural support to the cells and resulting epithelial tissue.

The epidermis consists of four morphologically and biochemically distinct layers. The basal layer of keratinocytes is in contact with the basement membrane, which separates the epidermis from the dermis. Basal cells are the only keratinocytes in intact skin capable of mitosis and, as such, are the source of all other keratinocytes in the epidermis. They attach to the substratum through hemidesmosomes and to adjacent cells through desmosomes and adherens junctions (reviewed in Jensen and Wheelock, 1996). Basal layer cells are columnar in shape and produce keratins K5 and K14.

The first suprabasal keratinocyte layer is the stratum spinosum, so named for the "spiny" appearance of the many desmosomal contacts between adjacent cells. Keratinocytes in this layer no longer produce K5 and K14 but, instead, synthesize differentiation-specific keratins K1 and K10. Cells begin to produce involucrin and epidermis-specific transglutaminases in the upper stratum spinosum. Morphologically, spinous cells are larger and more flattened than basal cells (reviewed in Holbrook, 1994).

Involucrin expression is localized to the cytoplasm of suprabasal and granular cells (Mansbridge and Knapp, 1987;

Murphy et al., 1984) of normal skin. Involucrin has also been shown to localize pericellularly in these layers, but tissues used for these immunohistochemistry experiments were not fixed, and it was hypothesized that the protein diffused to the cell borders during or after the sectioning process (Smola et al., 1993; Watt, 1983).

Transglutaminases are a family of calcium-dependent enzymes that catalyze the covalent cross-linking of proteins to each other or to polyamines (reviewed in Rice et al., 1994). The keratinocyte transglutaminase isozyme, $TG_K$, is membrane-bound in suprabasal epidermis and catalyzes the cross-linking of involucrin and at least six other membranous proteins to form the cornified envelope (CE) (reviewed in Rice et al., 1994). The CE is a highly stable insoluble protein structure formed beneath the plasma membrane that is resistant to detergents and reducing agents and confers strength and rigidity to the terminally differentiated cells of the uppermost epidermal layer. Many CE components, including $TG_K$, are synthesized in the stratum spinosum although the envelope is not formed until the cells transition from the stratum granulosum to the stratum corneum. $TG_K$ is also found in all subsequent layers of the epidermis (Michel et al., 1997; Mansbridge et al., 1987; Asselineau et al., 1989). The enzyme is inactive until, in the final stage of differentiation, a loss of membrane integrity results in an influx of calcium into the cell (Aeschlimann and Paulsson, 1994).

As keratinocytes differentiate further, they form the stratum granulosum. Cells of this layer are characterized by distinct electron-dense keratohyalin granules containing profilaggrin, the protein precursor of filaggrin (reviewed in Dale et al., 1994). Granular cells also contain lipid-filled granules that, during the transition zone between the stratum granulosum and stratum corneum, fuse with the plasma membrane and release their contents into the extracellular space, conferring hydrophobicity to the epidermal surface.

As the differentiating keratinocytes transition from the granular to the cornified layer, the profilaggrin is cleaved to yield filaggrin, which is involved in the alignment and aggregation via disulfide bonds of keratin bundles called macrofibrils (reviewed in Holbrook, 1994). Macrofibrils are the basic structural unit of the cornified envelope. In normal skin sections, filaggrin is localized in the granular layer, with some faint, continued staining in the cornified sheets (Michel et al., 1997; Asselineau et al., 1989; Mansbridge et al., 1987). It should be noted that antibodies against filaggrin detect profilaggrin as well as its cleavage products, which accounts for the strong, punctate staining pattern of the keratohyalin granules of the stratum granulosum.

The uppermost epidermal layer is the stratum corneum. Cells of this layer, having completed the differentiation process, have lost their nucleus and all metabolic function. They consist primarily of keratin filaments encased by the now-complete CE and overlying plasma membrane. Corneal cells are joined together by modified desmosomes and are ultimately sloughed off in sheets from the skin's surface.

Keratinocytes also produce cadherin adhesion molecules. The classical cadherins, N-, E-, and P-cadherin, are a subfamily of cadherins that localize to the adherens junctions and mediate cell-cell adhesion through homotypic interactions. These calcium-dependent, transmembrane glycoproteins play major regulatory roles in tissue formation and facilitate intercellular interactions. Cadherin complexes are also thought to participate in the transduction of intracellular signals through their association with the actin cytoskeleton (Knudsen et al., 1998). Keratinocytes produce both E- and P-cadherins. E-cadherin is found in all living layers of the epidermis (reviewed in Jensen and Wheelock, 1996) while P-cadherin is found in the stratum basale and immediately suprabasal cells.

The skin regenerates every 28 days (reviewed in Sams, 1996). As basal keratinocytes lose contact with the basement membrane they produce daughter cells that terminally differentiate as they move upward through the suprabasal layers to the skin surface. Terminal differentiation involves a series of biochemical and morphologic changes that result in a layer of dead, flattened squames that carries out the barrier and protective functions of the skin. These cornified cells are routinely sloughed off and replaced with newly differentiated cells, maintaining the controlled balance between proliferation and differentiation involved in tissue homeostasis.

Keratinocyte Culture

Cultivated cells isolated from disaggregated human skin have been used for over two decades to study keratinocyte growth and differentiation (reviewed in Leigh et al., 1994). Human foreskin keratinocytes cultured in the presence of a 3T3 mouse embryo fibroblast feeder layer or in serum-free medium formulations exhibit sustained growth for approximately 80 population doublings prior to senescence (reviewed in Leigh and Watt, 1994). Human keratinocytes cultured under these conditions can express differentiation-specific proteins, such as involucrin and keratins K1 and K10, in a position-specific manner (reviewed in Fuchs and Weber, 1994).

Although features of squamous differentiation and limited stratification are consistently observed in cultured keratinocyte monolayers, normal tissue architecture is not evident. The discovery that epidermal cells in traditional submerged culture grow optimally when plated on top of non-proliferating fibroblasts was a significant contribution to the study of keratinocyte cell biology (Rheinwald, 1980; reviewed in Fuchs, 1993). The use of this culturing system allowed investigators to serially cultivate keratinocytes for a wide range of purposes. Unfortunately, the submerged culture system allows for limited, aberrant stratification consisting of only a few layers of keratinocytes, which lack the specific morphological and biochemical characteristics of a true stratified epithelium. For example, several markers of normal epidermal differentiation are not produced in submerged culture, such as keratins 1 and 10 and the late stage marker, filaggrin (reviewed in Fuchs, 1993). Several factors limit this in vitro system. First, in vivo epidermis sits atop the dermis and receives its nutrients and growth signals via diffusion from the dermis through the basement membrane to the overlying basal cells. This imparts a polarity to the tissue that cannot be achieved in traditional submerged cell cultures that are fed through all upper surfaces to the bathing medium. Second, epithelial cells grown in this manner do not produce a basement membrane and lack exposure to its mesenchymal cues for normal differentiation and growth (reviewed in Fusenig, 1994). Third, while the fibroblast "feeder" layer promotes keratinocyte proliferation, the cultivation of cells in this manner results in the same aberrant or absent differentiation characteristics as is seen in cultures grown on a plastic substratum. This indicates that keratinocytes require a more complex mesenchyme of fibroblasts and extracellular matrix proteins to produce a functional epidermis. Accordingly, the traditional submerged culture system is appropriate only for relatively simplistic studies.

Several systems developed and tested over the past 20 years are designed to develop more in vivo-like keratinocyte culturing conditions. In 1979, collagen gels were first used as physiologic "rafts" upon which to grow keratinocytes at the air-medium interface (Bell et al., 1979; reviewed in Fusenig, 1994; Parenteau et al., 1992). This allowed the nutrients and growth factors from the medium to diffuse through the collagen to the basal layer of keratinocytes and exposed the uppermost keratinocyte layers to the air. These added in vivo-like conditions improved the histological architecture of the cultured epidermis. Full stratification and histological differentiation can be achieved using these three-dimensional "organotypic" culture methods, which have been continually modified to more closely recapitulate the in vivo growth environment.

In later organotypic systems, live fibroblasts were incorporated into collagen gels, keratinocytes were placed atop contracted collagen "rafts", and the entire raft was lifted to the air-medium interface (reviewed in Fusenig, 1994) to emulate intact skin, where resident dermal cells such as dermal fibroblasts are involved in signaling keratinocytes to produce a basement membrane and an epithelium with a significantly improved differentiation program (reviewed in Watt and Hertle, 1994). The viable fibroblasts provide valuable signals and promoted production by cultured keratinocytes of basement membrane proteins.

Keratinocyte Differentiation

In both intact skin and in organotypic culture, differentiating keratinocytes produce proteins unique to particular differentiation stages. The presence and localization of these protein markers can be detected using biochemical and immunohistochemical methods and used to determine whether an epithelial tissue is differentiating (stratifying) normally. The expression profiles of several such proteins are presented below.

The most well-studied proteins for determining epidermal differentiation are the keratins, most notably K5/14 and K1/10, which make up the intermediate filament network in epidermal keratinocytes. This network provides a cellular framework that extends from the nucleus to specific adhesion junctions called desmosomes and hemidesmosomes (reviewed in Fuchs and Cleveland, 1998). These cell-cell and cell-substratum interactions, when connected to keratin filaments, are responsible for anchoring keratinocytes to each other and to the underlying basement membrane. The K5/K14 pair of keratin filaments is expressed in the basal cells of stratified squamous epithelia (reviewed in Fuchs, 1993). As expected, K14 mRNA is present only in the basal layer of normal human epidermis (Stoler et al., 1988). As basal cells of the epidermis begin to differentiate, they downregulate their expression of K5/14 and begin to produce differentiation-specific keratins. The K1/K10 pair of keratin filaments is expressed in the suprabasal layers of the epidermis (reviewed in Fuchs, 1993). K1 and K10 are early markers of terminal differentiation as they are produced by keratinocytes upon leaving the basal layer. In samples of intact human skin, K1 is from the first suprabasal layer throughout the surface of the tissue (Stoler et al., 1988; Stark et al., 1999; Asselineau et al., 1989; Boukamp et al., 1990).

In primary human keratinocyte organotypic cultures, initiation of K1 protein synthesis is delayed relative to intact skin. Protein localization begins 5–8 cell layers above the basement membrane as opposed to 1–2 layers in normal skin samples. Induction of K1 production normalizes following transplantation of the organotypic cultures onto nude mice (Smola et al., 1993; Stark et al., 1999). These studies did not examine K1 mRNA expression.

Involucrin is localized to the suprabasal cell membranes in primary keratinocyte organotypic cultures, even in fixed tissue (Boukamp et al., 1990; Smola et al., 1993; Stark et al., 1999; Watt et al., 1987), and several groups also found that the membranous pattern remained after transplantation onto nude mice (Breitkreutz et al., 1997; Watt et al., 1987).

$TG_K$ expression seems to vary in organotypic cultures of normal human keratinocytes, first appearing either in the stratum spinosum or the stratum granulosum and continuing up through the stratum corneum (Michel et al., 1997; Stark et al., 1999).

Organotypic cultures of normal human keratinocytes also display localization of filaggrin in the granules of the uppermost strata of the epidermal tissue (Boukamp et al., 1990; Michel et al., 1997; Stark et al., 1999).

In addition to differentiation markers, one can also assess the structural and functional integrity of an epithelial tissue by monitoring for the presence and localization of adhesion proteins.

To date, neither of E- nor P-cadherin has been examined in organotypic culture of primary keratinocytes, although E-cadherin has been detected immunohistochemically in normal skin (Haftek et al., 1996).

Smola and coworkers (Smola et al., 1998) have clearly shown that organotypic cultures composed of normal dermal fibroblasts and keratinocytes develop a basement membrane zone capable of supporting cell type specific adhesion structures such as hemidesmosomes.

BRIEF SUMMARY OF THE INVENTION

The present invention is summarized in that a coculture of a human immortalized keratinocyte cells and human donor cells is advantageously employed as a chimeric skin for use in skin grafting and other plastic surgery methods.

Objects, features and advantages of the invention will become apparent upon consideration of the following description taken in conjunction with the accompanying drawings.

BRIEF DESCRIPTION OF THE SEVERAL VIEWS OF THE DRAWINGS

FIGS. 2A and B are NIKS$^{GFP}$ cells. FIGS. 2C and D are LAW-1 keratinocytes. FIGS. 2E and F are a 1:1 ratio of NIKS$^{GFP}$ and LAW-1-EP keratinocytes. FIGS. 2G and H are a 3:1 ratio. FIGS. 2A, C, E and G are hematoxylin and eosin stained. FIGS. 2B, D, F and H are Hoescht stained to view the cell nuclei.

FIGS. 5A and B indicate keratin-1. FIGS. 5C and D indicate transglutaminase-1. FIGS. 5E and F indicate filaggrin. FIGS. 5G and H indicate E-cadherin. FIGS. 5I and J indicate P-cadherin. FIGS. 5A, C, E, G and I are hematoxylin and eosin stained to view tissue histology. FIGS. 5B, D, F, H and J are visualized using an indirect immunofluorescence technique.

FIG. 7A is appearance in vivo. FIG. 7B is hematoxylin and eosin to view histology. FIG. 7C is GFP expression.

FIG. 8A is histology.

FIG. 9A is the chimeric graph in day 28.

DESCRIPTION OF THE INVENTION

Figure 1:
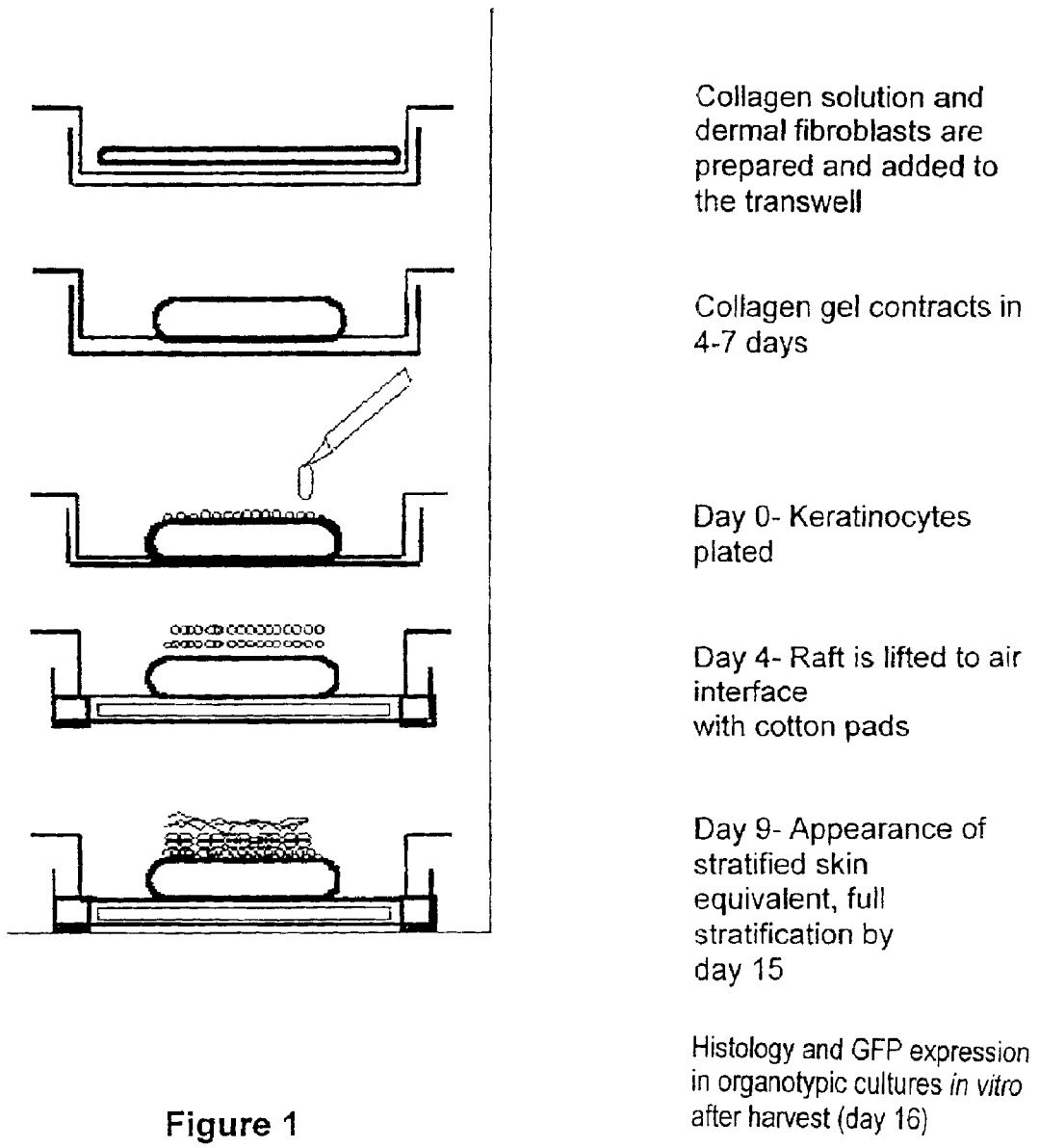
FIG. 1 is a flow chart of organotypic culture preparation.

The present invention involves using a combination of in vitro cultured conditionally immortal carrier human keratinocytes and donor patient-derived keratinocytes to form skin grafts. We disclose herein that such carrier keratinocytes derived from in vitro cell culture sources can be cocultured with donor patient keratinocytes using monolayer or organotypic culture methods to produce an engineered chimeric skin suitable for grafting. A conditionally immortal keratinocytes are keratinocytes that are immortal under defined growth conditions. A keratinocyte is considered immortal if it can be cultured under the defined growth conditions for more than 20 passages, preferably more than 30 passages, still more preferably more than 40 passages, and yet more preferably for more than 50 passages. In this application, the terms "conditionally immortal" and "immortal" are used interchangeably. The in vitro cultured conditionally immortal carrier human keratinocytes are allogeneic to the graft recipient. The donor or patient-derived keratinocytes are preferably autologous to the graft recipient.

In some preferred embodiments, the spontaneously immortalized NIKS (Near-Diploid Immortalized KeratinocyteS) cell line is utilized as the source of carrier keratinocytes. NIKS cells (ATCC CRL-12191) have not been exposed to mutagenic agents, possess wild-type p53 and Rb genes, retain cell type-specific growth requirements and differentiation properties, are non-tumorigenic in nude and SCID mice, are virus free, and recapitulate full skin architecture in monolayer and organotypic culture and respond to growth factors that regulate keratinocyte growth, such as EGF and TGF-$\beta$1. This is in contrast to HaCaT cells (Boelsma et al., 1999; Schoop et al., 1999) which at later passages exhibit anchorage independent growth, have high colony forming efficiency, reach high saturation densities, and do not require cell type-specific culture conditions for serial cultivation (Fusenig and Boukamp, 1998).

Unlike other spontaneously immortalized keratinocyte cell lines such as HaCaT, NIKS keratinocytes differentiate to the same extent and at the same rate as the parental BC-1-Ep keratinocytes in organotypic culture with dermal fibroblasts to form a stratified epithelium that is histologically identical to the parental BC-1-Ep cells and to other normal keratinocyte strains. The multilayered keratinizing epithelium is highly organized and exhibits features typical of intact skin such as hemidesmosomes, desmosomes, keratin tonofilaments, and keratohyalin granules. Both the parental and NIKS keratinocytes produce hemidesmosomes in organotypic culture suggesting that the synthesis, deposition, and assembly of extracellular matrix glycoproteins has occurred.

In standard monolayer- or organotypic coculture, NIKS cells do not overgrow the human keratinocytes, do not exhibit aberrant differentiation protein expression patterns (among those tested), and obey tissue compartment boundaries, neither dropping below the basement membrane nor acting like a tumor cell. NIKS cells do not cause aberrant replication of dermal fibroblasts in the collagen gel.

NIKS were originally cultured from neonatal foreskin and subsequently developed a spontaneous stable genetic addition of the long arm of chromosome 8 that allows these cells to have a significant survival advantage in culture. U.S. Pat. Nos. 5,989,837 and 6,214,567, incorporated herein by reference, disclose the creation and use of NIKS cells. See also, Allen-Hoffmann, B. L., et al., "Normal Growth and Differentiation in a Spontaneously Immortalized Near-Diploid Human Keratinocyte Cell Line, NIKS," J. Invest. Dermatol. 114:444–455, 2000, incorporated herein by reference, which describes suitable monolayer and organotypic culture conditions for conditionally immortal maintenance of the NIKS cells.

Such engineered chimeric monolayer and organotypic cell cultures and/or engineered chimeric skin equivalent tissue grafts would have the unique characteristics of providing immediate wound coverage and also providing autologous cells for late formal wound closure. The new skin equivalent tissue can be used, for example, as a skin replacement using an autologous (NIKS+patient cells), allogeneic (NIKS+unrelated cells on a patient), or xenogeneic graft (NIKS+pig cells or primate cells) for, e.g., wound closure (diabetic ulcers, skin burns, necrotizing skin disease, etc.) or cosmetic purposes (face lifts, other plastic surgery procedures). The chimeric skin equivalent tissue of the invention can be provided in sizes and thicknesses suitable for use in grafting methods and other methods in the manner in which the artisan skilled in such methods would use existing grafts and tissues.

The present invention is not limited, however, to the use of NIKS cells in chimeric coculture. Indeed, the present invention contemplates the use of a variety of other conditionally immortalized, nontumorigenic carrier cells and cell lines that form cornified envelopes when induced to differentiate and that undergo normal squamous differentiation and maintain cell type-specific growth requirements. Other sources of such cells can include keratinocytes and dermal fibroblasts biopsied from humans and cavaderic donors (Auger et al., In Vitro Cell. Dev. Biol.—Animal 36:96–103; U.S. Pat. Nos. 5,968,546 and 5,693,332, each incorporated herein by reference), neonatal foreskins (Asbill et al., Pharm. Research 17(9): 1092–97 (2000); Meana et al., Burns 24:621–30 (1998); U.S. Pat. Nos. 4,485,096; 6,039, 760; and 5,536,656, each of which is incorporated herein by reference), and immortalized keratinocytes cell lines such as NM1 cells (Baden, In Vitro Cell. Dev. Biol. 23(3):205–213 (1987)) and HaCaT cells (Boucamp et al., J. cell. Biol. 106:761–771 (1988)). Each of these cell lines can be cultured or genetically modified as described in more detail below. The scope of the invention also extends to use of cells and cell lines derived, directly or indirectly, from the aforementioned suitable cell types, including derivatives of NIKS cells, where such cells and cell lines retain the ability to function in the method of the invention.

In general, the method of the present invention is characterized by the following steps: One would obtain an in vitro carrier keratinocyte culture, preferably an organotypic culture of immortalized keratinocytes such as NIKS cells. One may wish to genetically manipulate the cultured keratinocytes. For example, the cells can be engineered to express or enhance expression of a protein or other gene product, or to suppress a protein or gene product. Other manipulations can include the knockin or knockout (ablation) of a gene or mutation of an existing gene or gene product. For example, in some preferred embodiments, either the carrier keratinocyte cells or patient derived cells are transfected or transformed with a gene of interest (for example, the gene encoding human Kruppel-like factor (GKLF) 4). In further preferred embodiments, the gene of interest is operably linked to promoter in an appropriate vector. In some preferred embodiments, tissue specific promoters such as the involucrin or transglutaminase 3 promoters are utilized. In other preferred embodiments, the expression of GKLF is driven by the inducible promoter system of the pTetOn plasmid (Clontech, Palo Alto, Calif.). In still other embodiments, a constitutive promoter can be used. It is contemplated that other mammalian expression vectors are suitable for use in the present invention, including, but not limited to, pWLNEO, pSV2CAT, pOG44, PXT1, pSG (Stratagene) pSVK3, pBPV, pMSG, pSVL (Pharmacia). Any other plasmid or vector can be used as long as it can replicate and remain viable in the host. In some preferred embodiments of the present invention, mammalian expression vectors comprise an origin of replication, a suitable promoter and enhancer, and any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites can be used to provide the required non-transcribed genetic elements. Additionally, the KLF 4 gene can be inserted via a retroviral vector. Transfection can be accomplished by any method known in the art, including but not limited to calcium-phosphate coprecipitation, electroporation, microparticle bombardment, liposome mediated transfection, or retroviral infection.

In still further embodiments, the graft is engineered to provide a therapeutic agent to a subject. The present invention is not limited to the delivery of any particular therapeutic agent. Indeed, it is contemplated that a variety of therapeutic agents can be delivered to the subject, including, but not limited to, enzymes, peptides, peptide hormones, other proteins, ribosomal RNA, ribozymes, and antisense RNA. These therapeutic agents can be delivered for a variety of purposes, including but not limited to the purpose of correcting genetic defects. In some particular preferred embodiments, the therapeutic agent is delivered for the purpose of detoxifying a patient with an inherited inborn error of metabolism (e.g., aminoacidopathesis) in which the graft serves as wild-type tissue. It is contemplated that delivery of the therapeutic agent corrects the defect. In some embodiments, the keratinocytes used to form the skin equivalent include a polynucleotide that encodes encode a therapeutic agent (e.g., insulin, clotting factor IX, erythropoietin, etc.) and the skin equivalent is grafted onto the subject. The therapeutic agent is then delivered to the patient's bloodstream or other tissues from the graft. In preferred embodiments, the polynucleotide that encodes the therapeutic agent is operably linked to a suitable promoter. The present invention is not limited to the use of any particular promoter. Indeed, a variety of promoters is contemplated, including, but not limited to, inducible, constitutive, tissue specific, and keratinocyte-specific promoters. In some embodiments, the nucleic acid encoding the therapeutic agent is introduced directly into the keratinocytes (i.e., by calcium phosphate co-precipitation or via liposome transfection). In other preferred embodiments, the nucleic acid encoding the therapeutic agent is provided as a vector and the vector is introduced into the keratinocytes by methods known in the art. In some embodiments, the vector is an episomal vector such as a plasmid. In other embodiments, the vector integrates into the genome of the keratinocytes. Examples of integrating vectors include, but are not limited to, retroviral vectors, adeno-associated virus vectors, and transposon vectors.

In still other embodiments, techniques such as homologous recombination can be used to knock in or knock-out genes. In particularly preferred embodiments, the genes for α-2 macroglobulin, or the major histocompatibility complex (MHC) genes are deleted or inactivated. Techniques and reagents for homologous recombination are described in U.S. Pat. Nos. 5,416,260; 5,965,977; and 5,981,214; each of which is incorporated herein by reference.

Next, one would identify a patient and isolate cells for coculture. For cultivating human keratinocytes in monolayer culture, a tissue sample is obtained. Keratinocytes are isolated from human skin or other stratified squamous epithelia. Keratinocyte cultures are established by plating aliquots of a single cell suspension in the presence of mitomycin C-treated Swiss mouse 3T3 fibroblasts as previously described (Allen-Hoffmann and Rheinwald, 1984). The standard keratinocyte culture medium is composed of a mixture of Ham's F-12 medium:Dulbecco's modified Eagle's medium (DME), (3:1, final calcium concentration 0.66 mM) supplemented with 2.5% fetal calf serum (FCS), 0.4 µg/ml hydrocortisone (HC), 8.4 ng/ml cholera toxin (CT), 5 µg/ml insulin (Ins), 24 µg/ml adenine (Ade), 10 ng/ml epidermal growth factor (EGF), 100 units penicillin and 100 µg/ml streptomycin (P/S). The cells are routinely subcultured at weekly intervals at $3 \times 10^5$ cells per 100-mm tissue culture dish (approximately a 1:25 split) with a mitomycin C-treated feeder layer. Recombinant human EGF and transforming growth factors-β1 (TGF-β1) are obtained from R & D Systems (Minneapolis, Minn.).

To produce a chimeric culture of donor keratinocytes and carrier keratinocytes, preferably NIKS keratinocytes, the desired ratio of donor keratinocytes and carrier keratinocytes is used at the time of subculture or at any other time during the culture process. For example, NIKS cells can be added to an adherent donor keratinocyte culture, donor keratinocytes can be added to an adherent NIKS monolayer culture, or the carrier cells and donor keratinocytes can be mixed together at time of subculture.

In some preferred embodiments for cultivation of the carrier keratinocyte cells (e.g., NIKS cells) and patient keratinocytes in organotypic culture, a collagen base is formed by mixing normal human fibroblasts, with Type I collagen in Ham's F-12 medium containing 10% FCS and P/S. The collagen base is allowed to contract for 5 days to form contracted collagen rafts. The patient keratinocytes and the NIKS keratinocytes are plated on the contracted collagen rafts at $3.5 \times 10^5$ cells in 50 µl of a mixture of Ham's F-12:DME, (3:1, final calcium concentration 1.88 mM) supplemented with 0.2% FCS, 0.4 µg/ml HC, 8.4 ng/ml CT, 5 µg/ml Ins, 24 µg/ml Ade, and P/S. Cells are allowed to attach for 2 hours before flooding culture chamber with media (day 0). On days 1 and 2 cells are re-fed. On day 4, cells are lifted to the air interface with cotton pads and switched to cornification medium containing Ham's F-12:DME, (3:1, final calcium concentration 1.88 mM) supplemented with 2% FCS, 0.4 µg/ml HC, 8.4 ng/ml CT, 5 µg/ml Ins, 24 µg/ml Ade, and P/S. Cells are fed cornification medium every 3 days until complete stratafication is achieved (approximately 15 days). One can identify successful monolayer culture by visual presence of keratinocytes in the culture dish. Successful organotypic culture is identified by the observing the ratios of patient-derived keratinocytes to carrier keratinocytes.

The ratios of patient-derived keratinocytes to carrier keratinocytes exemplified herein are not intended to be limiting. Indeed, based on the guidance given herein, it is clear that a variety of ratios can be used in the present invention. Accordingly, in some embodiments, a suitable ratio of patient-derived keratinocytes to carrier keratinocytes ranges from about 0.5%:99.5% to about 80%:20%, preferably from about 10%:90% to about 60%:40%; and most preferably a ratio of about 20%:80%.

A skin graft of the present invention will have the tissue architecture and differentiation and adhesion markers of normal skin Advantageously, a skin graft of the present invention can be grown faster than skin grafts made from patient-derived skin.

Figure 5:
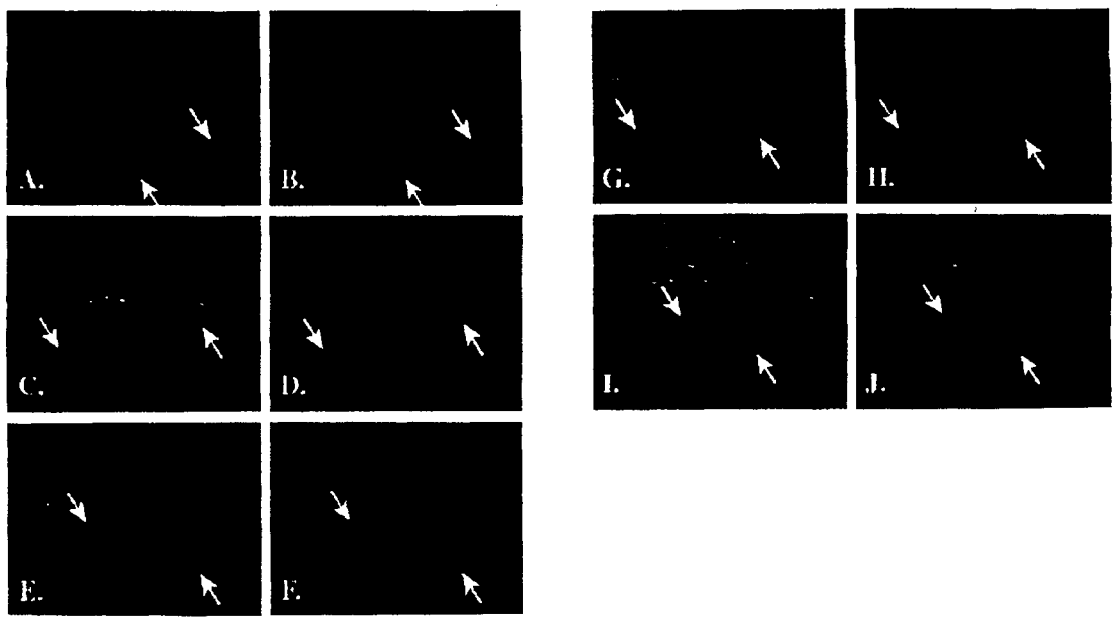
FIGS. 5A–J are a set of cross-sections describing immunohistochemical analysis of differentiation markers and adhesion molecules.

Organotypic chimeric cocultures of donor and carrier keratinocytes, and resulting skin grafts of the present invention, display a tissue architecture that closely resembles the architecture of normal skin and organotypic human keratinocyte cultures substantially as described in the Background of the Invention, supra and as shown in FIG. 5, taking into account the typical variations observed in organotypic cultures. For example, organotypic chimeric cocultures of primary human keratinocytes and NIKS cells were paraffin-embedded, sectioned, and stained with hematoxylin and eosin for histological examination. The cocultures exhibit a discrete stratum basale consisting of columnar basal cells. The overlying stratum spinosum is composed of several larger, progressively flattened cell layers. The upper layers display a granular layer having hematoxylin-stained keratohyalin granules.

The cultures exhibit normal distribution of cell-type specific proteins associated with various stages of squamous differentiation. The localization of differentiation markers was visualized using indirect immunofluorescence. The early stage differentiation marker keratin 1 appears as diffuse cytoplasmic staining in all cultures, with expression being initiated in the first or second suprabasal cell layer and continuing upward through the stratum.

Immunofluorescent staining shows a diffuse cytoplasmic protein localization of involucrin beginning in the first several suprabasal cell layers. NIKS cultures exhibit identical spatial localization of involucrin at 8, 11, and 13 days as at 21 days (Loertscher et al., 2000). Prior analyses of intact, normal human skin samples have demonstrated the expected cytoplasmic localization of involucrin (Mansbridge and Knapp, 1987; Murphy et al., 1984). Our data shows involucrin protein localized in the cytoplasmic compartment, as expected. This finding supports our claim of normal, in vivo-like differentiation of chimeric, organotypic cultures of human keratinocytes and NIKS keratinocytes.

The intermediate differentiation marker $TG_K$ exhibits identical localization patterns and intensity in chimeric, organotypic NIKS and human keratinocyte cultures (FIG. 5). Its distinct, honeycomb-like appearance reflects the localization of the membrane-bound $TG_K$ enzyme.

The late stage differentiation marker filaggrin is localized to the keratohyalin granules in the cells of the stratum granulosum of NIKS and primary keratinocyte rafts, as indicated by its punctate staining pattern (FIG. 5). Chimeric organotypic cultures of human keratinocytes and NIKS keratinocytes displayed normal spatial localization of filaggrin (FIG. 5) at 15 days.

Immunohistochemistry was also used to determine the presence and localization of E- and P-cadherin. In the cocultures of the invention, E-cadherin appears in the regions of cell-cell contact in all cultures, with expression beginning in the immediate suprabasal layer and continuing up through the living strata (FIG. 5). The P-cadherin expression pattern is also similar in all cultures, but is initiated in the stratum basale and continues only through the first several suprabasal layers (FIG. 5). These findings mirror those observed in intact skin and demonstrate that chimeric, organotypic human keratinocyte and NIKS keratinocyte cultures produce an appropriate pattern of cadherin molecules as compared to organotypic cultures of human keratinocytes alone and/or intact human skin.

The present invention will be more fully understood upon consideration of the following non-limiting Examples.

EXAMPLES

Methods

Cell Culture Methods:

Donor keratinocytes (GS-1-EP, LAW-1-EP) were isolated from newborn human foreskins. Samples were obtained after circumcision under the approval of the hospital's Human Subjects Committee and Institutional Biosafety Committee. GS-1-EP, LAW-1-EP and NIKS keratinocyte cultures were established by plating aliquots of a single cell suspension in the presence of mitomycin C-treated Swiss mouse 3T3 fibroblasts (mito-3T3) as previously described (6). The standard keratinocyte culture medium was composed of a mixture of Ham's F-12 medium:Dulbecco's modified Eagle's medium (DME), (3:1, final calcium concentration 0.66 mM) supplemented with 2.5% fetal calf serum (FCS), 0.4 µg/ml hydrocortisone (HC), 8.4 ng/ml cholera toxin (CT), 5 µg/ml insulin (Ins), 24 µg/ml adenine (Ade), 10 ng/ml epidermal growth factor (EGF), 100 units penicillin and 100 µg/ml streptomycin (P/S). Cells were subcultured at weekly intervals at $3 \times 10^5$ cells per 100-mm tissue culture dish (approximately a 1:25 split) with a mito-3T3 feeder layer.

Generation of Green Fluorescent Protein Expressing NIKS ($NIKS^{GFP}$):

Plasmid DNA was prepared using the Endotoxin Free Maxiprep Kit (Qiagen, Valencia, Calif.). pGreenLantern (Gibco-BRL, Rockville, Md.) and pcDNA3neo (Invitrogen, Carlsbad, Calif.) were linearized using the restriction enzymes XmnI and BglII (Promega, Madison, Wis.) respectively. A total of 20 µg DNA (15 µg pGreenLantern and 5 µg pcDNA3neo) was used for the transfection of NIKS cells at a ratio of 3:1 pGreenLantern to pcDNA3neo. NIKS were plated at a density of $3 \times 10^5$ cells onto a mito-3T3 feeder layer in 100 mm dishes. Cells were given 48 hours to adhere at which time the mito-3T3 layer was removed with 0.5 mM EDTA. NIKS cells at passage 30–40 were transfected using the polycationic lipid GeneFECTOR (VennNova, Miami, Fla.). The transfection mix was made by adding linearized plasmid DNA and GeneFECTOR to a final volume of 500 µl with sterile milli-Q water for each 100 mm dish. The transfection mix was swirled gently and incubated for 15 minutes at room temperature. NIKS cells were rinsed twice with DME and re-fed with 5 ml's of DME. Five hundred µl of transfection mix was added to each 100 mm plate in a drop-wise fashion and cells were incubated for 5 hours at 37° C. under 5% $CO_2$. The media was removed and cells were rinsed twice with DME and re-fed with serum-containing media. Cells were viewed 24 hours post-transfection with an IX-70 inverted fluorescence microscope (Olympus, Melville, N.Y.) equipped with a GFP short band pass filter to observe GFP expression prior to analysis by Flow-Activated Cell Sorting (FACS).

Assessment of Chimeric Culturing on Keratinocyte Growth Rates:

$NIKS^{GFP}$, LAW-1-EP, and GS-1-EP were plated separately and mixed at a ratio of 1:1, 1:10 and 1:100 ($NIKS^{GFP}$:GS-1-EP or LAW-1-EP). Cells were plated at a final concentration of $10^5$-cells/60 mm dish in triplicate on a 3T3 feeder layer and counted four days later. Experiments were repeated twice with $NIKS^{GFP}$ and GS-1-EP and once with LAW-1-EP. Results were also normalized for the differences in plating efficiency between different strains of keratinocytes.

Organotypic Culture Methods:

Organotypic cultures were grown as previously described (7) in transwell culture chambers with the following changes: a collagen base was formed by mixing normal human neonatal fibroblasts, strain CI-1-F, with Type I rat tail tendon collagen in Ham's F-12 medium containing 10% FCS and P/S. The collagen base was allowed to contract for 4 to 7 days. LAW-1-EP, GS-1-EP and NIKS$^{GFP}$ (passage 47) were plated separately and at the following ratios: (90% NIKS$^{GFP}$, 10% LAW-1-EP), (87.5% NIKS$^{GFP}$, 12.5% LAW-1-EP), (75% NIKS$^{GFP}$, 25% LAW-1-EP), (50% NIKS$^{GFP}$, 50% LAW-1-EP). A total of 3.5×10$^5$ cells were plated on the contracted collagen base in 50 μl of a mixture of Ham's F-12:DME, (3:1, final calcium concentration 1.88 mM) supplemented with 0.2% FCS, 0.4 μg/ml HC, 8.4 ng/ml CT, 5 μg/ml Ins, 24 μg/ml Ade, and P/S. Cells were allowed to attach for 2 hours before the culture chamber was flooded with media (day 0). On day 2 cells were re-fed. On day 4, cells were lifted to an air/media interface with cotton pads and switched to cornification medium containing Ham's F-12:DME, (3:1, final calcium concentration 1.88 mM) supplemented with 2% FCS, 0.4 μg/ml HC, 8.4 ng/ml CT, 5 μg/ml Ins, 24 μg/ml Ade, and P/S. Cells were fed cornification medium every 3 days and were harvested on Day 16 (FIG. 1).

Histology and Immunohistochemistry Methods:

Specimens were fixed for 2 hours with 1% paraformaldehyde. In preparation for freezing, cultures were submerged in 20% sucrose/PBS overnight at 4° C. before being frozen in OCT in an isopentane bath chilled over liquid nitrogen. Cryopreserved cultures and graft biopsies were serially sectioned (5 μm), mounted on glass slides, stained with hematoxylin and eosin, and viewed with an Olympus IX-70 inverted microscope. Images were acquired with a DEI-750 camera (Optronics Engineering) and Image-Pro Plus software (Media Cybernetics, Silver Spring, Md.). For immunohistochemical analysis of differentiation markers, cryopreserved tissues were serially sectioned (5 μm), mounted on glass slides, and fixed briefly in −20° C. acetone. Sections were washed with PBS, blocked with 3% normal goat serum (Sigma, St. Louis, Mo.), and incubated with primary antibody for 1 hour. Primary antibodies include: anti-keratinocyte transglutaminase (1:100 dilution) (Biomedical Technologies Inc., Stoughton, Mass.), anti-filaggrin (1:250 dilution) (Biomedical Technologies Inc., Stoughton, Mass.), anti-keratin-1 (1:50 dilution) (Novo Castra, Newcastle upon Tyne, UK), anti-E-cadherin (1:80 dilution) (Transduction Laboratories, Lexington, Ky.), anti-P-cadherin (1:20 dilution) (Transduction Laboratories, Lexington, Ky.), and anti-involucrin (1:5000 dilution) (Sheibani, 1994). Sections were then incubated with Alexa 594-conjugated immunoglobulin-G (1:1000 dilution) (Molecular Probes, Eugene Oreg.), and counterstained with Hoechst 33258 (1 μg/ml). All incubations occurred at room temperature except incubation of the anti-P-cadherin primary antibody, which occurred at 37° C. Sections were viewed with an Olympus IX-70 inverted microscope equipped with FITC and Hoechst band pass filters. Images were acquired with a DEI-750 camera (Optronics Engineering) and Image-Pro Plus software (Media Cybernetics, Silver Spring, Md.).

Grafting of Chimeric Organotypic Cultures:

Animal experiments using athymic Nu/Nu mice (5 week old) obtained from Harlan Sprague Dawley were performed in accordance with the University of Wisconsin's Animal Research regulations and approved by the Animal Care and Use Committee. Mice were anesthetized using 3% isoflurane for induction of anesthesia and were then maintained with 1.5%–2.5% isoflurane for the duration of the procedure. Toe pinch was performed on mice to assess level of anesthesia prior to beginning grafting procedure. Post-operative pain management was alleviated with buprenorphine (0.05 mcg/kg subcutaneously). Antibiotics (sulfamethoxazole and trimethoprim 200 mg/40 mg per 5 ml) were placed in drinking water (10 ml/250 ml $H_2O$) for the first three days post-operatively. Mice were cleansed with 4% chlorhexidine gluconate (Zeneca Pharmaceuticals, Wilmington Del.) and rinsed with sterile saline prior to incision. Skin defects were made on the dorsum of the mice. The organotypically-cultured grafts were placed dermal side down and secured with nylon sutures. Aquaphor gauze (Beiersdorf-Jobst Inc, Rutherford College NC) impregnated with bacitracin zinc (500 units) and polymyxin b sulfate (10,000 units) ointment (E. Fougera, Melville, N.Y.) was stapled over the grafts. Xeroform gauze (3% bismuth tribromophenate) (Sherwood Medical, St Louis Mo.) was stapled over the top of the graft. An additional layer of spandex fabric was stapled in place to discourage mice from removing bandages. Mice were observed daily for one week post-operatively at which point the mice were re-anesthetized as previously described and bandages were removed. Graft biopsies were obtained at 7, 14 and 28-day intervals after euthanasia in a $CO_2$ chamber.

Results

Figure 2:
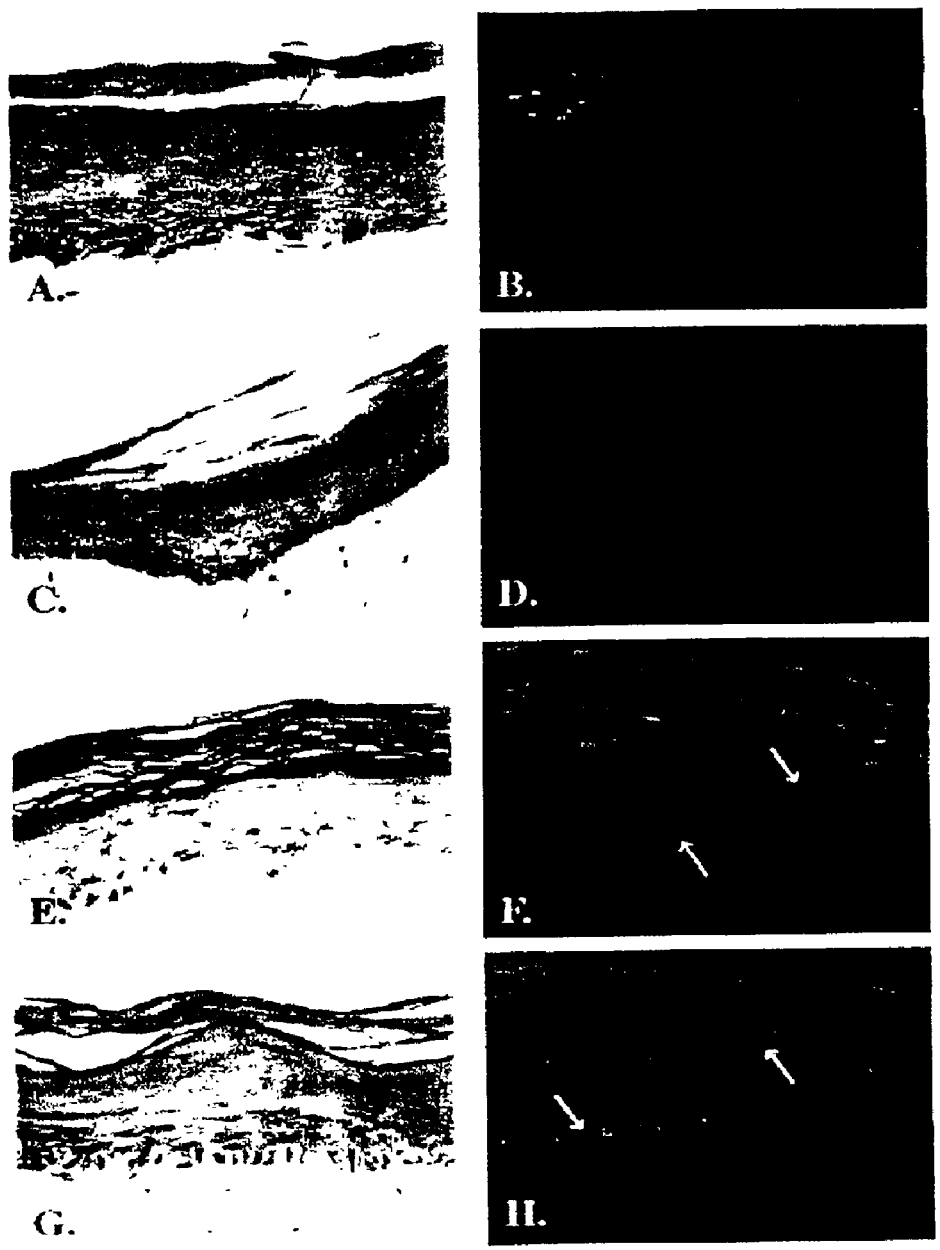
FIGS. 2A–H are a set of cross-sections of the cocultured tissue.

Generation of Green Fluorescent Protein Expressing NIKS (NIKS$^{GFP}$):

We genetically engineered the NIKS cells to express the exogenous gene green fluorescent protein (GFP). These were placed into sub-culture at weekly intervals at 3×10$^5$ cells per 100-mm tissue culture dish with a mito-3T3 feeder layer. NIKS$^{GFP}$ were an important cellular reagent for many facets of this project and allowed for visualization under the fluorescent microscope (FIG. 2). NIKS$^{GFP}$ have growth and differentiation characteristics identical to that of the untransfected NIKS cells.

Figure 3:
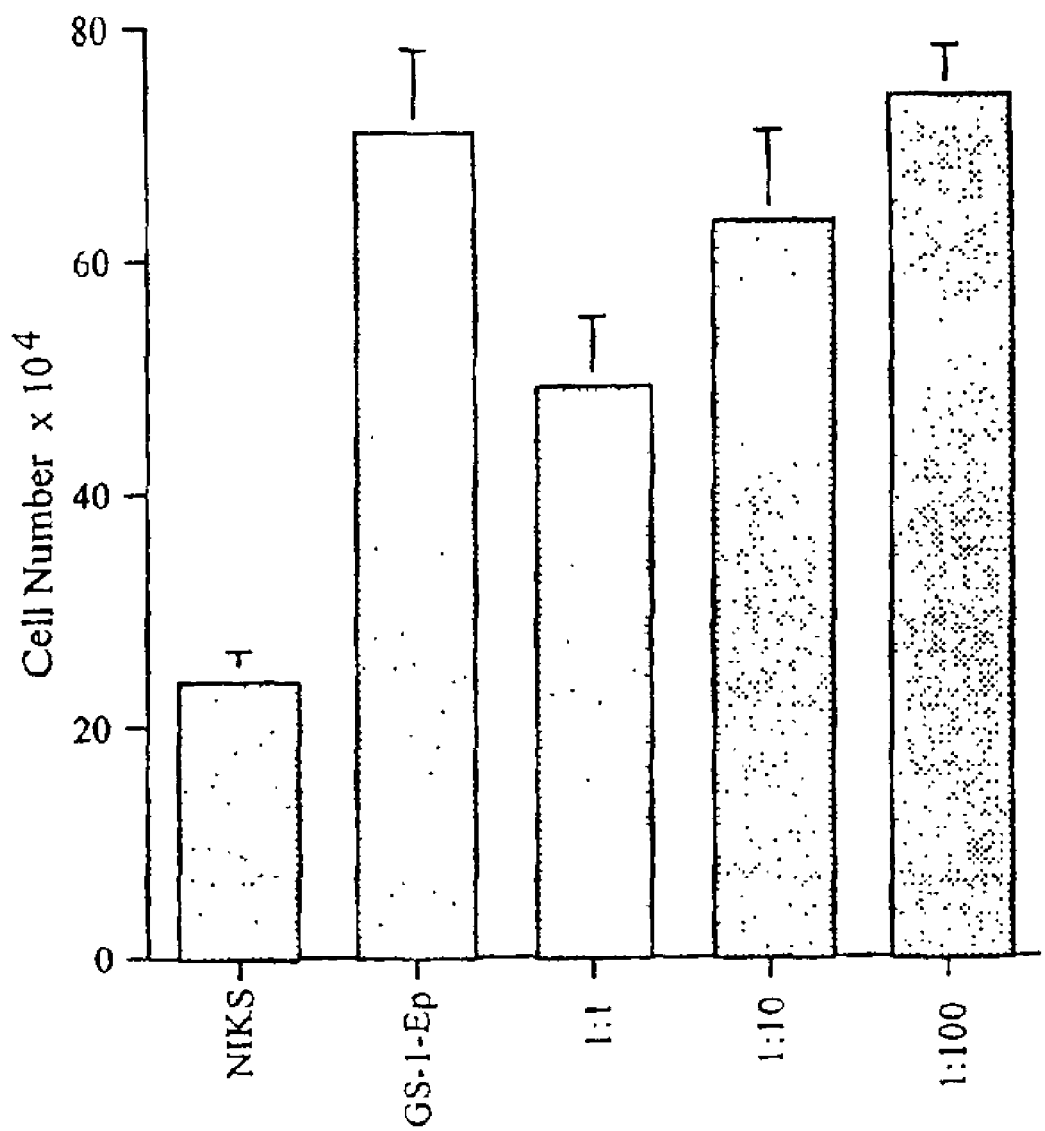
FIG. 3 is a bar graph of the growth rate of monolayer culture.
Figure 4:
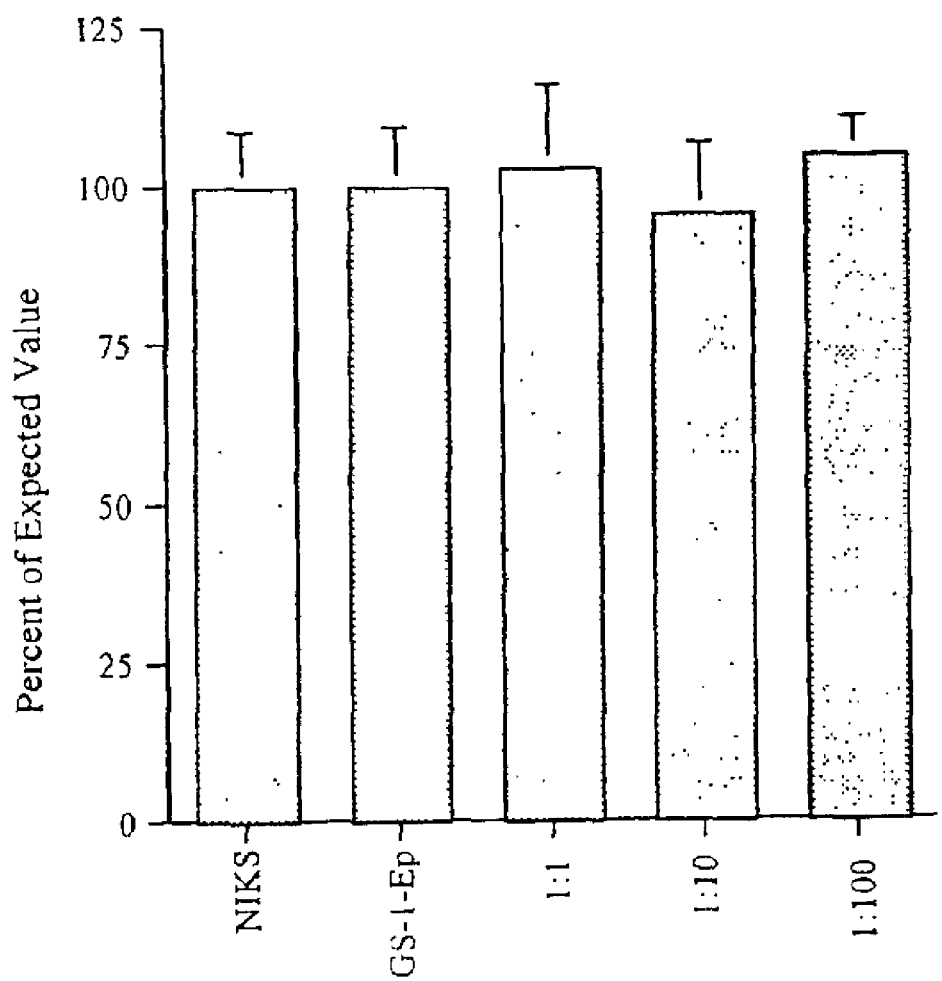
FIG. 4 is a bar graph of normalized growth rate in monolayer culture.

Assessment of Chimeric Culturing on Keratinocyte Growth Rates:

Monolayer culture techniques documented formation of contiguous chimeric epithelial sheets of GFP-expressing NIKS cells and donor human keratinocytes. Co-culturing of NIKS$^{GFP}$ cells with other strains of keratinocytes did not affect the growth rate of either strain of keratinocyte in monolayer culture. NIKS$^{GFP}$ subcultures reach 90% confluence at a slower rate than either LAW-1-EP or GS-1-EP, i.e. they have a slower growth rate in monolayer culture (FIG. 3). Normalized results show no effect of chimeric culturing at ratios of 1:1, 1:10, and 1:100 on growth rates in monolayer culture (FIG. 4).

Histology and Immunohistochemical Analysis of Organotypic Cultures:

In vitro organotypic cultures of chimeric NIKS$^{GFP}$/LAW-1-EP demonstrate normal growth and architecture at ratios of 1:1 and 3:1 (FIG. 2). Organotypic cultures of NIKS$^{GFP}$ and GS-1-EP also demonstrated normal architecture by hematoxylin and eosin staining at ratios of 1:1, 10:1, and 100:1. Immunohistochemical analysis of differentiation markers and adhesion molecules is shown in FIG. 5. Keratin 1 and the membrane-associated differentiation marker, transglutaminase-1, were found in a suprabasal position. Transglutaminase-1 is clearly seen in rings associated with the cell membrane. Filaggrin staining is appropriately limited to the granular layer. Analysis of adhesion molecules shows that P-cadherin expression is appropriately limited to the basal layer and E-cadherin expression is located throughout the epidermis.

Figure 6:
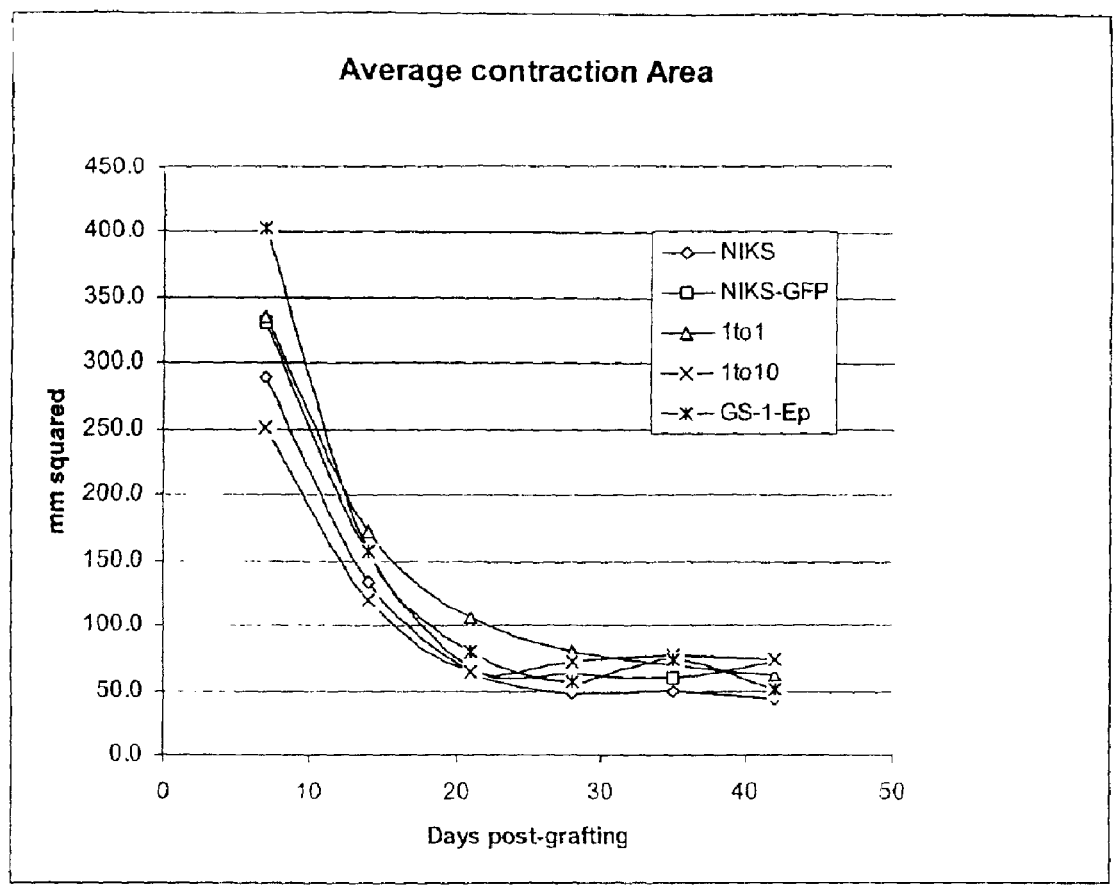
FIG. 6 is a graph of the average wound contraction area.
Figure 7:
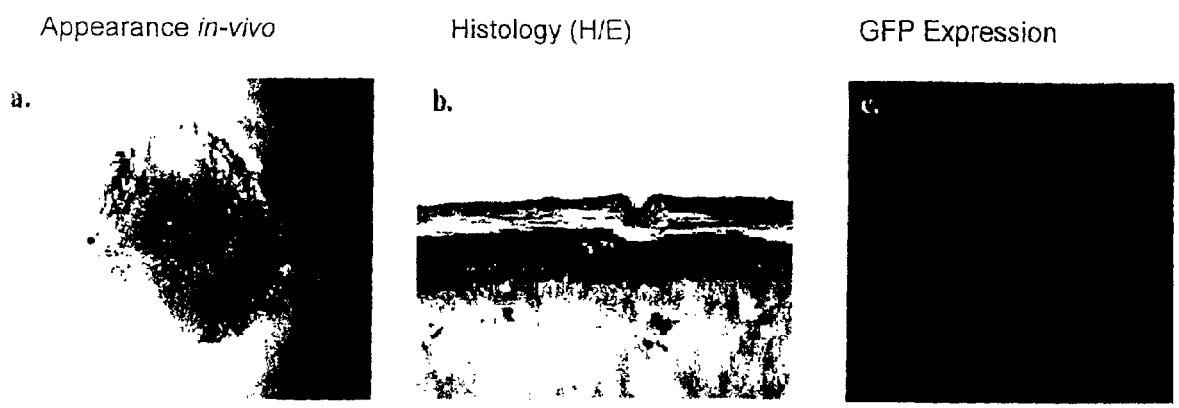
FIG. 7A–C is a set of views of biopsy sections.
Figure 8:
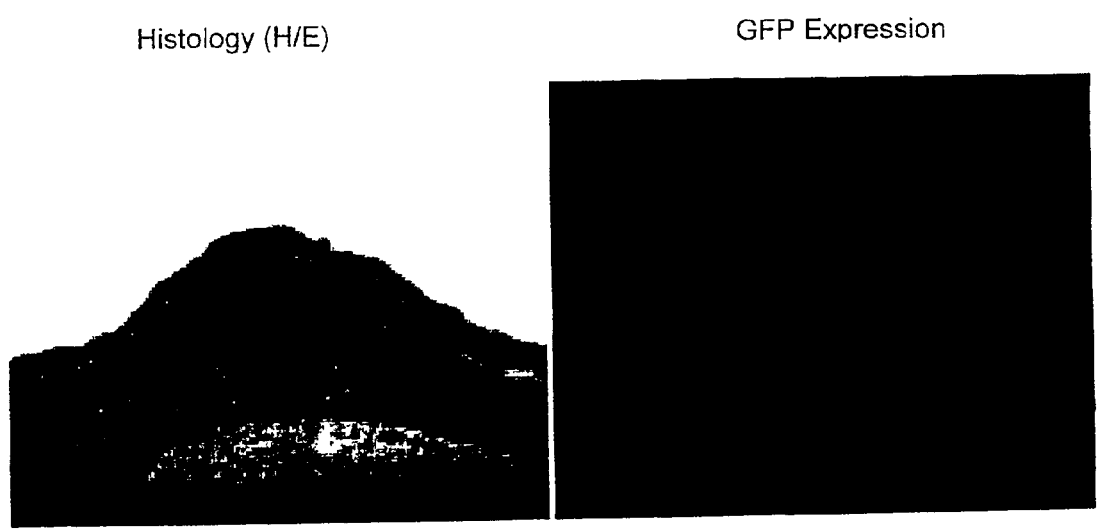
FIGS. 8A and B is a set of views of biopsy sections 28 days after grafting.
FIG. 8B is GFP expression.
Figure 9:
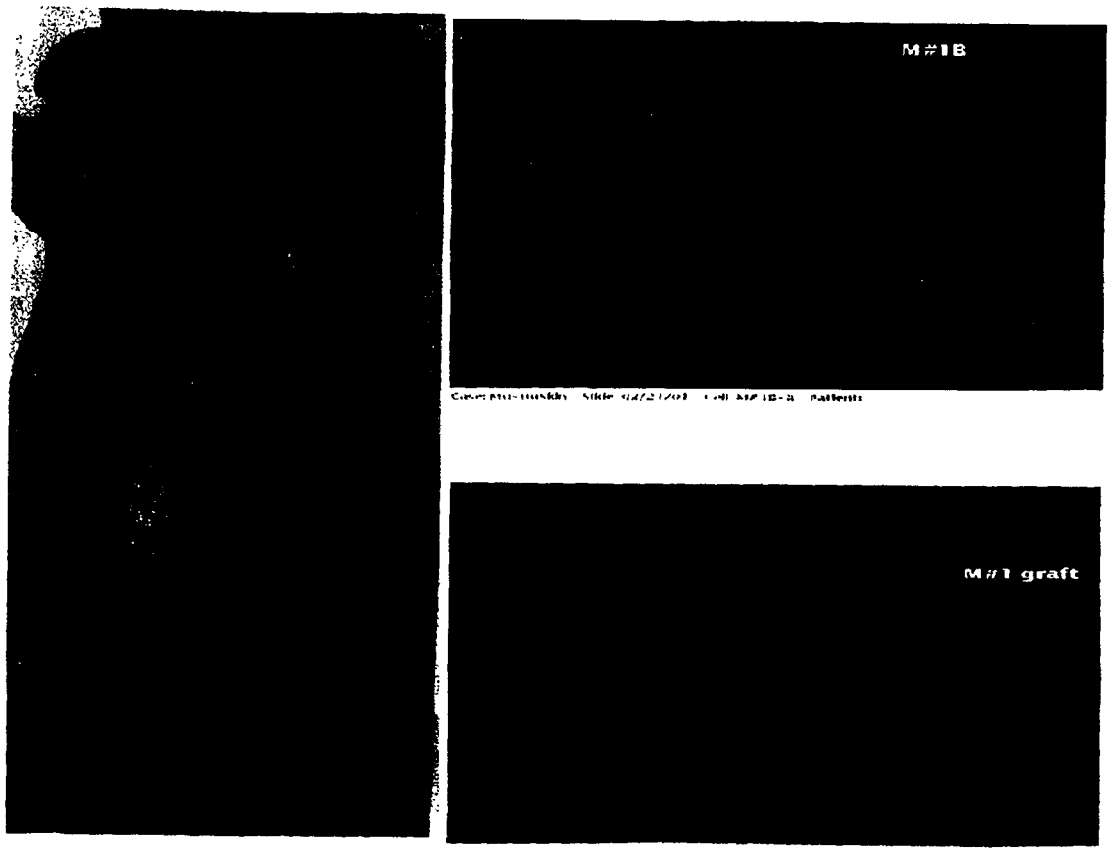
FIGS. 9A, B and C is a set of views analyzing the x/y centromere.
FIGS. 9B and C are x/y centromere analysis.

Grafting of Chimeric Organotypic Cultures:

The workability of the cultured grafts was noteworthy. They were easily handled and easily transferred to a wound bed. Grafts did not tear with suturing or stapling and were successfully meshed at ratios of 2:1 with a non-crushing mesher (Brennan Medical, St. Paul, Minn.). Significant initial graft contraction occurred with stabilization in graft size by day 20 (FIG. 6). Graft biopsies demonstrated normal tissue architecture and GFP expression at 7 and 28 days (FIGS. 7, 8). X-Y centromere analysis confirmed the presence of human cells (FIG. 9).

Discussion

Patients with catastrophic burn injury have insufficient donor site available for recipient site coverage. Current techniques available for skin resurfacing can be life-saving for burn patients, although significant problems remain. The major hindrance to the use of autologous cultured keratinocytes is the delay required for clonal expansion. Often the patients develop uncontrolled sepsis before cultured grafts become available, thus a reduction in the culture time required for creation of autologous skin grafts would be a major improvement in patient care.

The inventors here demonstrated that NIKS cells can be cocultured with donor human keratinocytes in an organotypic culture and used as an engineered tissue suitable for skin grafting. Rapid organotypic growth using 90% allogeneic cells interspersed with 10% autologous keratinocytes would allow for earlier wound coverage. Slower permanent resurfacing of the skin would occur with the autologous keratinocytes as the allogeneic cells reject. Such grafts would have the unique characteristics of providing immediate wound coverage and also providing autologous cells for late formal wound closure.

The feasibility of this unique approach has been previously demonstrated in animal models. Chimerically cultured keratinocytes from different strains of mice (BALB/c and C3H/He) grafted onto either experimental mouse strain resulted in long-term survival of syngeneic keratinocytes and rejection of the allogeneic keratinocytes (3). This has also been shown using chimeric keratinocyte cultures containing 98% allogeneic and only 2% syngeneic cells (8). Additionally, chimeric syngeneic-xenogeneic (mouse-human) cultured keratinocytes grafted onto mice resulted in complete resurfacing of the skin with syngeneic cells as the xenogeneic cells were eliminated (4).

A major hindrance to the clinical advancement of this technique has been the unavailability of an established allogeneic keratinocyte line. The significant survival advantage associated with the NIKS cell line makes it a well-suited allogeneic cell line for chimeric culturing with a patient's autologous keratinocytes. Autologous keratinocytes passaged at a lower confluence and added to NIKS in culture would allow significant timesaving to occur. Chimeric culturing of NIKS with a patient's autologous keratinocytes would lead to earlier wound coverage with an engineered tissue that provides autologous cells for late formal wound closure.

We have shown that when cocultured with donor keratinocytes in a chimeric fashion that there is no overgrowth of one cell type to the other. We have further shown that the expression and localization of the late-stage differentiation markers keratin 1, transglutaminase 1, and filaggrin and the adhesion molecules E-Cadherin and P-Cadherin are identical to those of intact skin. NIKS is a preferred cell line to be used as a permanent allogeneic donor keratinocyte line.

To date the NIKS cell line has not been characterized for expression of major histocompatibility complex antigens (MHC), and its rejection characteristics are unknown. Unlike skin grafts, organotypic cultures do not contain highly antigenic epithelial or vascular endothelial elements such as Langerhans cells and capillaries. It is possible that NIKS would not be rejected when placed onto humans. Chimeric cultured skin grafts on an immunocompetent animal model would address xeno-tranplant rejection, but would not definitively define whether NIKS cells would be rejected in a clinical setting. If NIKS were passively eliminated by rejection, resurfacing would occur with autologous cells. If NIKS were not rejected, the cell line could potentially function as a universal donor skin. At a minimum, chimerically cultured NIKS would act as a temporary biological covering and a delivery vehicle for autologous keratinocytes.

The lack of a capillary plexus also is also significant, as revascularization of the cultured skin is not accomplished by inosculation to pre-existing capillaries, but rather by angiogenesis. The delay in revascularization can be responsible for the rapid early reduction in graft size seen in this study, although an alternative explanation would be that rapid wound contraction is characteristic of athymic mice. Genetic engineering techniques have been used to address the delay in revascularization inherent in cultured skin.

NIKS are readily amenable to molecular genetic techniques for the creation of stable cell lines as evidenced by the successful creation of NIKS$^{GFP}$. Since the NIKS cells can be genetically engineered, it is feasible to incorporate genetically engineered NIKS keratinocytes into chimeric cultures to promote the wound-healing characteristics of chimeric grafts. Furthermore, NIKS cell lines can be created with specific genetic profiles such as expression of growth factors. As a result, a wide variety of customized NIKS-based tissue products could be generated.

The present invention is not intended to be limited to the preceding disclosure but rather to encompass all such modifications and variations as come within the scope of the appended claims.

References

1. Boyce, S. T., et al., Cultured skin substitutes combined with Integra Artificial Skin® to replace native skin autograft and allograft for the closure of excised full-thickness burns, *J. Burn Care Rehabil.* 20:453–461, 1999.
2. Cairns, B. A., et al., The biotechnological quest for optimal wound closure, *Arch. Surg.* 128:1246–1252, 1993.
3. Suzuki, T., Ui, K., Shioya, N. and Ihara, S., Mixed cultures compromising syngeneic and allogeneic mouse keratinocytes as a graftable skin substitute, *Transplantation* 59:1236–1241, 1995.
4. Rouabhia, M., Permanent skin replacement using chimeric epithelial cultured sheets comprising xenogeneic and syngeneic keratinocytes, *Transplantation* 61:1290–1300, 1996.
5. Allen-Hoffmann, B. L., et al., Normal growth and differentiation in a spontaneously immortalized near-diploid human keratinocyte cell line, NIKS, *J. Invest. Dermatol.* 114:444–455, 2000.
6. Allen-Hoffmann, B. L. and Rheinwald, J. G., Polycyclic aromatic hydrocarbon mutagenesis of human epidermal keratinocytes in culture, *Proc. Natl. Acad. Sci. USA* 81:7802–7806, 1984.
7. Parenteau, N. L., et al., The organotypic culture of human skin keratinocytes and fibroblasts to achieve form and function, *Cytotechnology* 9:163–171, 1992.
8. Larochelle, F., Ross, G. and Rouabhia, M., Permanent skin replacement using engineered epidermis containing fewer than 5% syngeneic keratinocytes, *Lab. Invest.* 78:1089–1099, 1998.
9. Vogt, P. M., et al., Genetically modified keratinocytes transplanted to wounds reconstitute the epidermis, *Proc. Nat. Acad. Sci. USA* 91:9307–9311, 1994.
10. Supp, D. M., Supp, A. P., Bell, S. M. and Boyce, S. T., Enhanced vascularization of cultured skin substitutes genetically modified to overexpress vascular endothelial growth factor, *J. Invest. Dermatol.* 114:5–13, 2000.
11. Supp, D. M. and Boyce, S. T., Overexpression of vascular endothelial growth factor accelerates early vascularization and improves healing of genetically modified cultured skin substitutes, *J. Burn Care Rehabil.* 23:10–20, 2002.

I claim:

1. A chimeric skin comprising an immortalized human keratinocyte cell in coculture with donor keratinocytes, wherein the skin comprises normal tissue architecture and differentiation markers of stratified squamous epithelia and wherein expression and location of late-stage differentiation markers are typical of intact human skin.

2. The skin of claim 1, wherein the donor keratinocytes are of human origin.

3. The skin of claim 1 wherein the immortalized keratinocytes are spontaneously immortalized keratinocytes.

4. The skin of claim 1 wherein the immortalized keratinocytes are ATCC CRL-12191.

5. The skin of claim 1, wherein the immortalized keratinocytes are genetically modified.

6. The skin of claim 5, wherein at least one genetically modified gene or gene product is expressed or enhanced.

7. The skin of claim 5 wherein expression of at least one genetically modified gene or gene product is suppressed.

8. A method of creating a chimeric skin, comprise the steps of:
   (a) obtaining a culture of immortalized human keratinocyte cells and donor keratinocytes from a patient;
   (b) co-culturing the immortalized keratinocytes and patient keratinocytes, such that a chimeric skin is formed, wherein the skin comprises normal tissue architecture and differentiation markers of stratified squamous epithelia and wherein expression and location of late-stage differentiation markers are typical of intact human skin.

9. The method of claim 8, wherein the donor keratinocytes are of human origin.

10. The method of claim 8 wherein the immortalized keratinocytes are spontaneously immortalized keratinocytes.

11. The method of claim 8 wherein the immortalized keratinocytes are ATCC CRL-12191.

12. The method of claim 8 further comprising the step of genetically modifying at least one of the immortalized keratinocytes and the donor keratinocytes.

13. A method of treating a patient in need of skin grafting, comprising the steps of:
   (a) obtaining the skin of claim 1;
   (b) preparing a patient for the receipt of a skin graft, and
   (c) grafting the skin onto the patient.

14. An organotypic coculture comprising immortalized human keratinocytes and donor keratinocytes, wherein the coculture comprises normal tissue architecture and differentiation markers of stratified epithelia and wherein expression and location of late-stage differentiation markers are typical of intact human skin.

15. The organotypic coculture of claim 14 wherein the donor keratinocytes are of human origin.

16. The organotypic coculture of claim 14 wherein the immortalized keratinocytes are spontaneously immortalized keratinocytes.

17. The organotypic coculture of claim 14 wherein the immortalized keratinocytes are ATCC CRL-12191.

18. The organotypic coculture of claim 14 wherein the immortalized keratinocytes are genetically modified.

19. The organotypic coculture of claim 18, wherein at least one genetically modified gene or gene product is expressed or enhanced.

20. The organotypic coculture of claim 18 wherein expression of at least one genetically modified gene or gene product is suppressed.

* * * * *